(12) United States Patent
Falkovich et al.

(10) Patent No.: US 11,484,649 B2
(45) Date of Patent: Nov. 1, 2022

(54) VALVE ASSEMBLY FOR DRUG DELIVERY DEVICE

(71) Applicant: Becton, Dickinson and Company, Franklin Lakes, NJ (US)

(72) Inventors: Margarita Falkovich, Paramus, NJ (US); Venkateswaran Santhanam, Newark, DE (US); Peter Skutnik, Midland Park, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 77 days.

(21) Appl. No.: 16/887,133

(22) Filed: May 29, 2020

(65) Prior Publication Data

US 2020/0376195 A1   Dec. 3, 2020

Related U.S. Application Data

(60) Provisional application No. 62/854,587, filed on May 30, 2019.

(51) Int. Cl.
| | |
|---|---|
| *A61M 5/168* | (2006.01) |
| *A61M 5/142* | (2006.01) |
| *A61M 5/145* | (2006.01) |
| *A61M 39/22* | (2006.01) |

(52) U.S. Cl.
CPC ...... *A61M 5/16813* (2013.01); *A61M 5/1454* (2013.01); *A61M 5/14244* (2013.01); *A61M 39/22* (2013.01); *A61M 2005/14252* (2013.01); *A61M 2205/0266* (2013.01)

(58) Field of Classification Search
CPC .......... A61M 5/16813; A61M 5/14244; A61M 5/1454; A61M 39/22; A61M 2005/14252; A61M 2205/0266; A61M 2005/1585; A61M 5/3202; A61M 2005/2474; A61M 5/3293; A61M 5/158; A61M 5/31536; A61M 5/31566; A61M 5/31571; A61M 2005/2026
See application file for complete search history.

(56) References Cited

U.S. PATENT DOCUMENTS

2017/0028132 A1*  2/2017  Cronenberg ........ A61M 5/2466
2017/0354788 A1   12/2017 Quinn et al.

FOREIGN PATENT DOCUMENTS

| CA | 3020337 A1 | 10/2017 | |
|---|---|---|---|
| WO | 2013155153 A1 | 10/2013 | |
| WO | 2014179774 A1 | 11/2014 | |
| WO | WO-2019183013 A1 * | 9/2019 | ......... A61B 1/00068 |

* cited by examiner

*Primary Examiner* — Theodore J Stigell
*Assistant Examiner* — Rachel T. Smith
(74) *Attorney, Agent, or Firm* — The Webb Law Firm

(57) ABSTRACT

A valve assembly for a drug delivery device includes a valve housing having a first side and a second side positioned opposite from the first side, a cannula having a first end and a second end positioned opposite the first end, a pierce plate having a body and a piercing member extending from the body, with the body defining a coiled elongate member, and a valve boot connected to the valve housing and defining an interior space. The valve boot is configured to move from a pre-use position where the first end of the cannula and the piercing member of the pierce plate are received within the interior space to a use position where the piercing member of the pierce plate and the first end of the cannula extend outside of the valve boot and the interior space.

9 Claims, 13 Drawing Sheets

VALVE ASSEMBLY FOR DRUG DELIVERY DEVICE

CROSS-REFERENCE TO RELATED APPLICATION

This application claims priority to U.S. Provisional Application Ser. No. 62/854,587, filed May 30, 2019, which is hereby incorporated by reference in its entirety.

BACKGROUND OF THE INVENTION

Field of the Invention

The present disclosure relates generally to a drug delivery device and, in particular, to a valve assembly for a drug delivery device.

Description of Related Art

Various types of automatic injection or drug delivery devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

In one aspect or embodiment, a valve assembly for a drug delivery device includes a valve housing having a first side and a second side positioned opposite from the first side, a cannula having a first end and a second end positioned opposite the first end, with the cannula defining a central passageway, a pierce plate including a body and a piercing member extending from the body, with the body formed by a coiled elongate member and the piercing member defining a central passageway configured to receive the cannula, and a valve boot connected to the valve housing and defining an interior space. The valve boot is configured to move from a pre-use position where the first end of the cannula and the piercing member of the pierce plate are received within the interior space to a use position where the piercing member of the pierce plate and the first end of the cannula extend outside of the valve boot and the interior space.

The valve assembly may further include a valve sleeve defining a cannula space, with the valve sleeve configured to move from a pre-use position where the first end of the cannula is received within the cannula space to a use position where the first end of the cannula extends outside of the valve sleeve and the cannula space. The valve sleeve may be formed from an elastomeric material. The valve sleeve may include a first cylindrical portion having a convex tip, a second portion extending from the first portion, and a third frustoconical portion extending from the second portion. The valve boot may be formed from an elastomeric material. The valve boot may include a projection extending radially inward, with the pierce plate engaged with the projection of the valve boot. The coiled elongate member has a first end and a second end axially spaced from the first end, the second end of the coiled elongate member configured to move toward the first end of the coiled elongate member. The coiled elongate member may be frustoconical. The coiled elongate member may include a first frustoconical portion and a second frustoconical portion, with the first frustoconical portion having a larger angle than the second frustoconical portion. The piercing member may be connected to the second end of the coiled elongate member. The piercing member may be connected to the second end of the coiled elongate member via an adhesive or welding. The coiled elongate member may be formed from a metal wire. The metal wire may be formed from a shape memory alloy. The shape memory alloy may be Nitinol.

In a further aspect or embodiment, a drug delivery device includes a housing, a cartridge received within the housing, the cartridge configured to receive a medicament, a drive assembly received within the housing and configured to engage the cartridge and dispense medicament from the cartridge, a needle actuator assembly received within the housing, with the needle actuator assembly including a patient needle configured to pierce a patient's skin, and a valve assembly including a valve housing having a first side and a second side positioned opposite from the first side, a cannula having a first end and a second end positioned opposite the first end, with the cannula defining a central passageway, a pierce plate comprising a body and a piercing member extending from the body, with the body formed from a coiled elongate member and the piercing member defining a central passageway configured to receive the cannula, and a valve boot connected to the valve housing and defining an interior space. The valve boot is configured to move from a pre-use position where the first end of the cannula and the piercing member of the pierce plate are received within the interior space to a use position where the piercing member of the pierce plate and the first end of the cannula extend outside of the valve boot and the interior space.

The drug delivery device may further include a valve sleeve defining a cannula space, with the valve sleeve configured to move from a pre-use position where the first end of the cannula is received within the cannula space to a use position where the first end of the cannula extends outside of the valve sleeve and the cannula space. The coiled elongate member may have a first end and a second end axially spaced from the first end, with the second end of the coiled elongate member configured to move toward the first end of the coiled elongate member. The piercing member may be connected to the second end of the coiled elongate member. The piercing member may be connected to the second end of the coiled elongate member via an adhesive or welding. The coiled elongate member may be a shape memory alloy wire.

In another aspect or embodiment, a valve assembly for a drug delivery device includes a valve housing having a first side and a second side positioned opposite from the first side, a cannula having a first end and a second end positioned opposite the first end, the cannula defining a central passageway, a valve boot connected to the valve housing and defining an interior space, with the valve boot configured to move from a pre-use position where the first end of the cannula is received within the interior space to a use position where the first end of the cannula extends outside of the valve boot and the interior space, and a valve sleeve defining a cannula space, with the valve sleeve configured to move from a pre-use position where the first end of the cannula is received within the cannula space to a use position where the first end of the cannula extends outside of the valve sleeve and the cannula space.

The valve sleeve may be formed from an elastomeric material. The valve sleeve may include a first cylindrical portion having a convex tip, a second portion extending from the first portion, and a third frustoconical portion extending from the second portion. The second portion of the valve sleeve may include a frustoconical section and a cylindrical section. The third portion of the valve sleeve may include at least one recessed portion configured to facilitate a collapse and deformation of the valve sleeve. The valve sleeve may be formed from a rubber material. The valve boot may be formed from an elastomeric material. The valve assembly may further include a pierce plate including a body and a piercing member extending from the body, with the piercing member of the pierce plate received within the interior space of the valve boot when the valve boot is in the pre-use position, and with the piercing member of the pierce plate extending outside of the valve boot and the interior space when the valve boot is in the use position.

In a further aspect or embodiment, a drug delivery device includes a housing, a cartridge received within the housing, with the cartridge configured to receive a medicament, a drive assembly received within the housing and configured to engage the cartridge and dispense medicament from the cartridge, a needle actuator assembly received within the housing, with the needle actuator assembly comprising a patient needle configured to pierce a patient's skin, and a valve assembly as described in any of the aspects or embodiments above.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION

Figure 1:
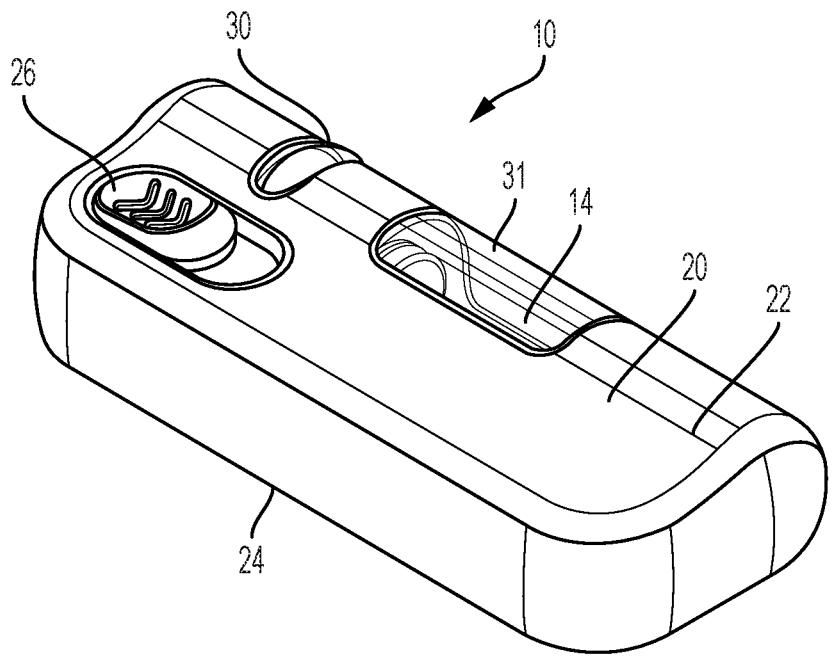
FIG. 1 is a perspective view of a drug delivery system according to one aspect or embodiment of the present application.
Figure 2:
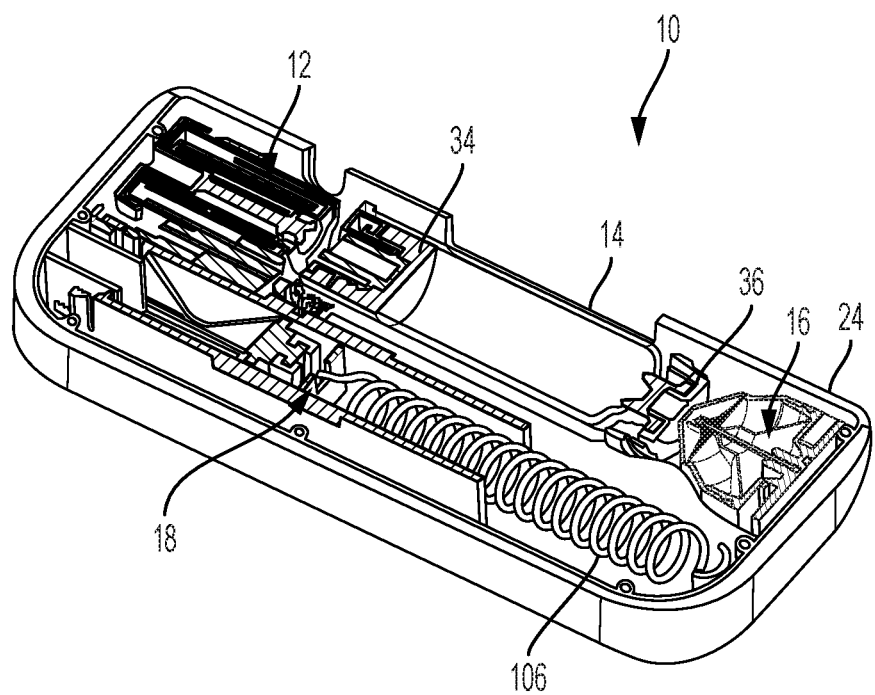
FIG. 2 is a perspective, cross-sectional view of the drug delivery system of FIG. 1.
Figure 3:
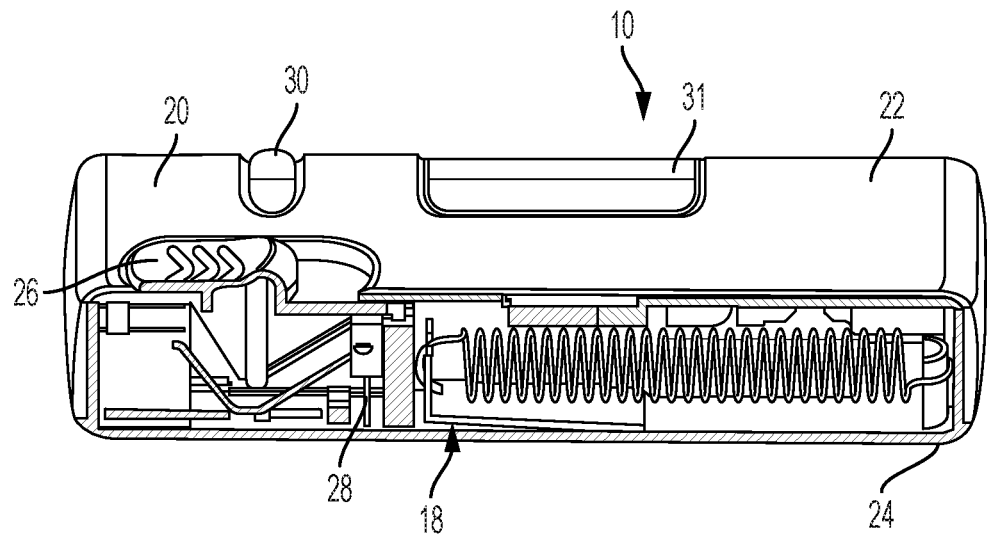
FIG. 3 is a front, cross-sectional view of the drug delivery system of FIG. 1.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-16, a drug delivery system 10 includes a drive assembly 12, a container 14, a valve assembly 16, and a needle actuator assembly 18. The drive assembly 12, the container 14, the valve assembly 16, and the needle actuator assembly 18 are at least partially positioned within a housing 20. The housing 20 includes a top portion 22 and a bottom portion 24, although other suitable arrangements for the housing 20 may be utilized. In one aspect, the drug delivery system 10 is an injector device configured to be worn or secured to a user and to deliver a predetermined dose of a medicament provided within the container 14 via injection into the user. The system 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The system 10 may deliver the medicament at a fixed pressure to the user with the rate being variable. The general operation of the system 10 is described below in reference to FIGS. 1-16.

Referring again to FIGS. 1-16, the system 10 is configured to operate through the engagement of an actuation button 26 by a user, which results in a needle 28 of the needle assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. The operation of the system 10 is also shown and described in U.S. Publication No. 2017/0354788, which is hereby incorporated by reference in its entirety. The housing 20 of the system 10 includes an indicator window 30 for viewing an indicator arrangement 32 configured to provide an indication to a user on the status of the system 10 and a container window 31 for viewing the container 14. The indicator window 30 may be a magnifying lens for providing a clear view of the indicator arrangement 32. The indicator arrangement 32 moves along with the needle actuator assembly 18 during use of the system 10 to indicate a pre-use status, use status, and post-use status of the system 10. The indicator arrangement 32 provides visual indicia regarding the status, although other suitable indicia, such an auditory or tactile, may be provided as an alternative or additional indicia.

Figure 4:
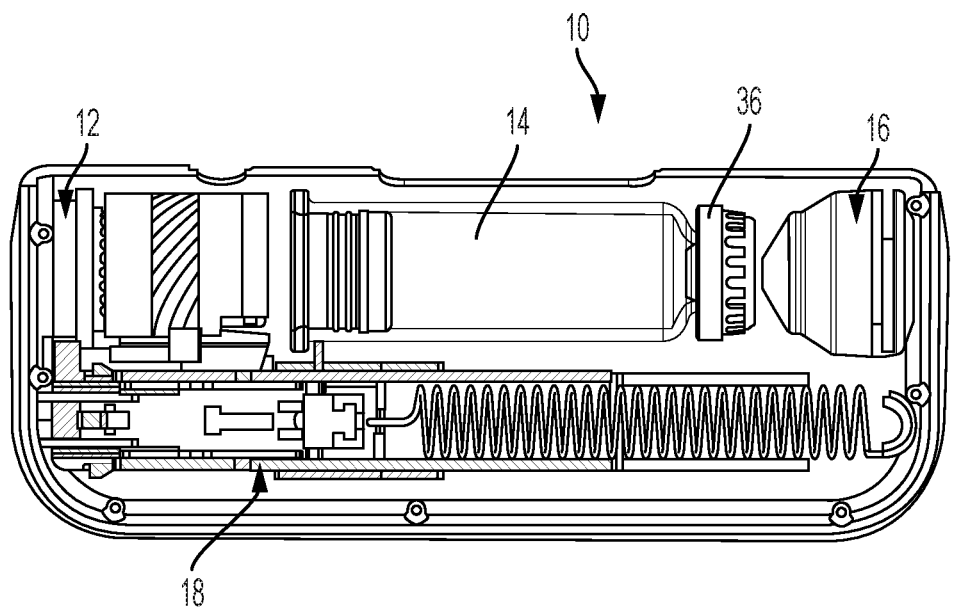
FIG. 4 is a top view of the drug delivery system of FIG. 1, showing a top portion of the housing removed and the drug delivery system in a pre-use position.
Figure 5:
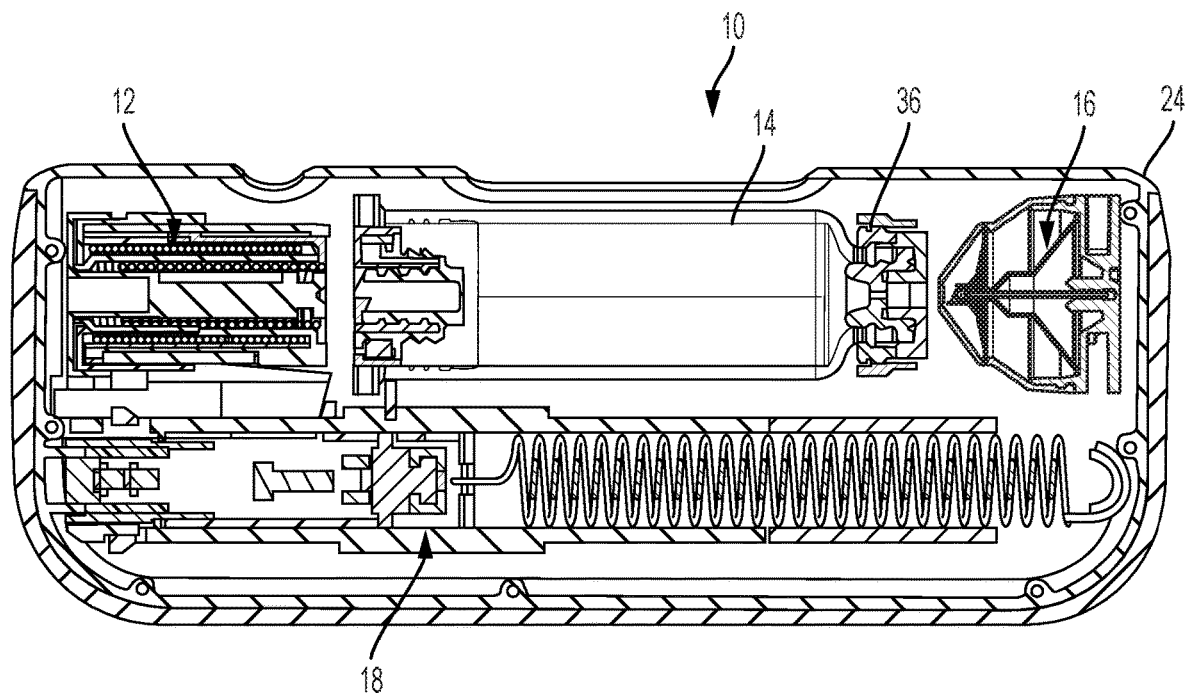
FIG. 5 is a top, cross-sectional view of the drug delivery system of FIG. 1, showing the drug delivery system in a pre-use position.
Figure 6:
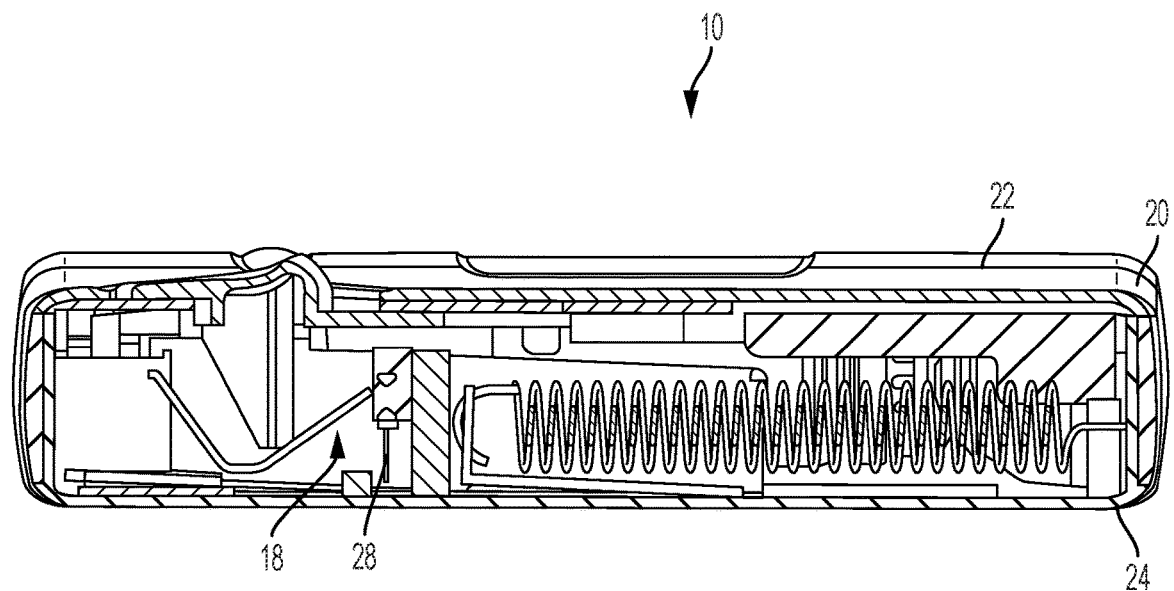
FIG. 6 is a front, cross-sectional view of the drug delivery system of FIG. 1, showing the drug delivery system in a pre-use position.
Figure 7:
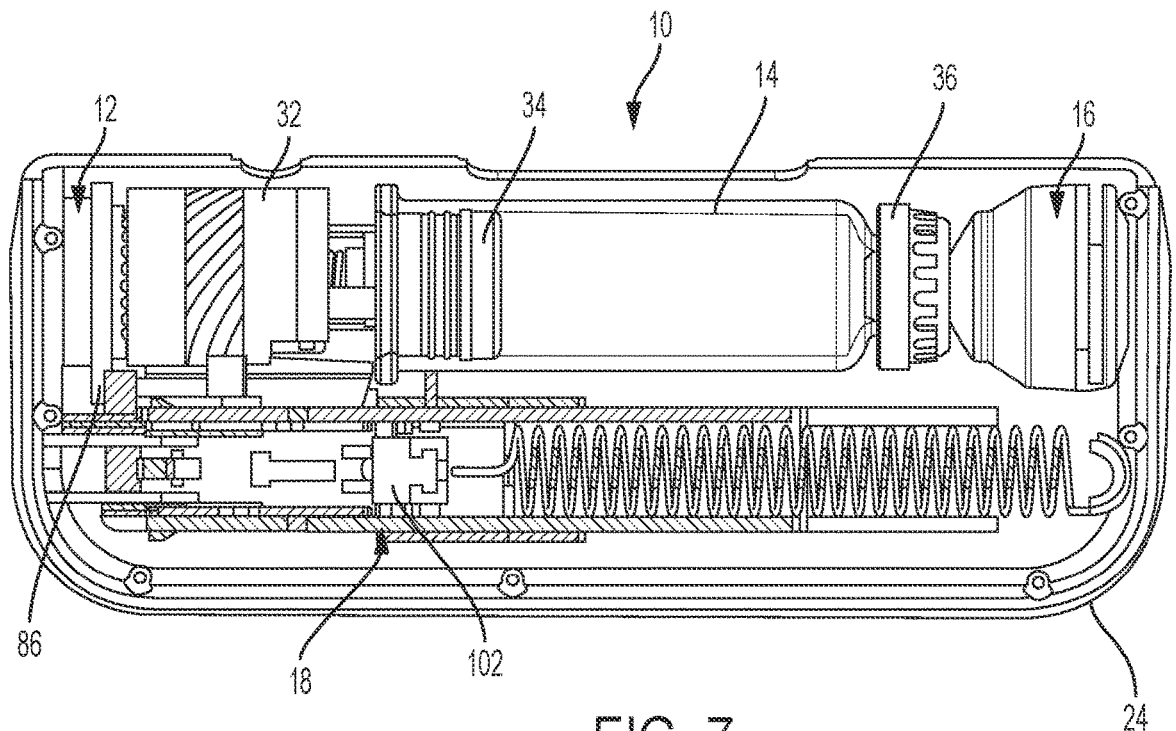
FIG. 7 is a top view of the drug delivery system of FIG. 1, showing a top portion of the housing removed and the drug delivery system in an initial actuation position.
Figure 8:
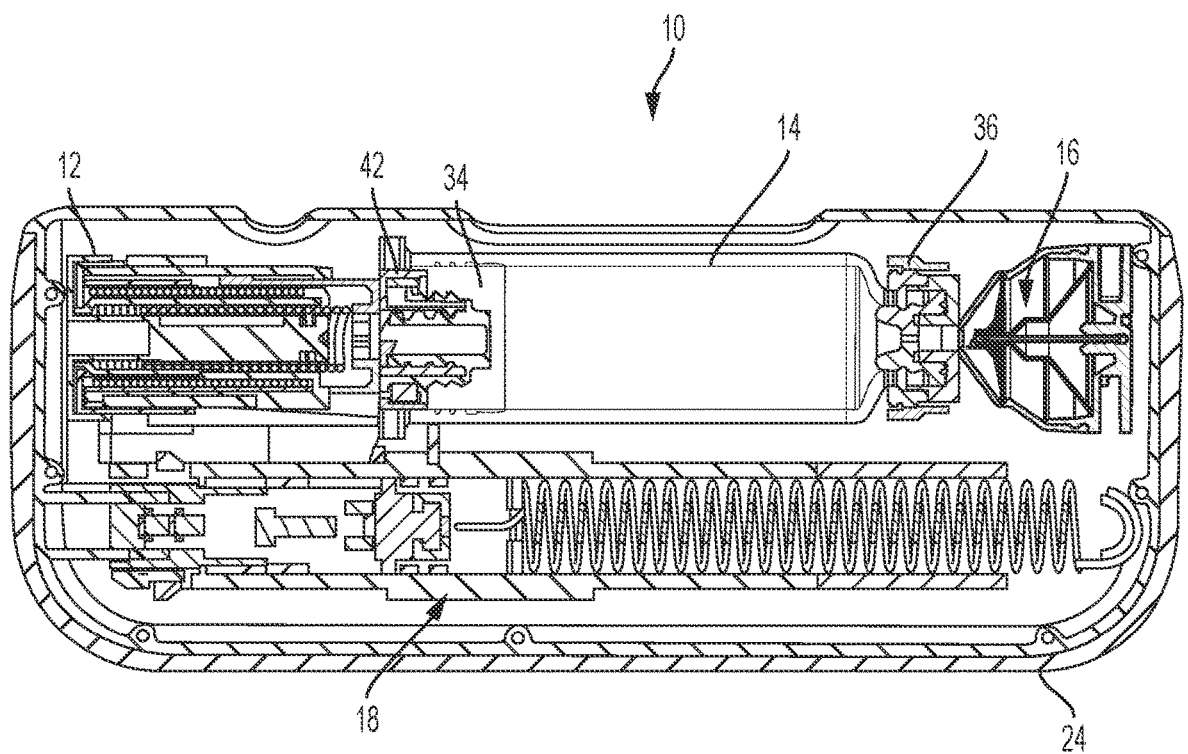
FIG. 8 is a top, cross-sectional view of the drug delivery system of FIG. 1, showing the drug delivery system in an initial actuation position.
Figure 9:
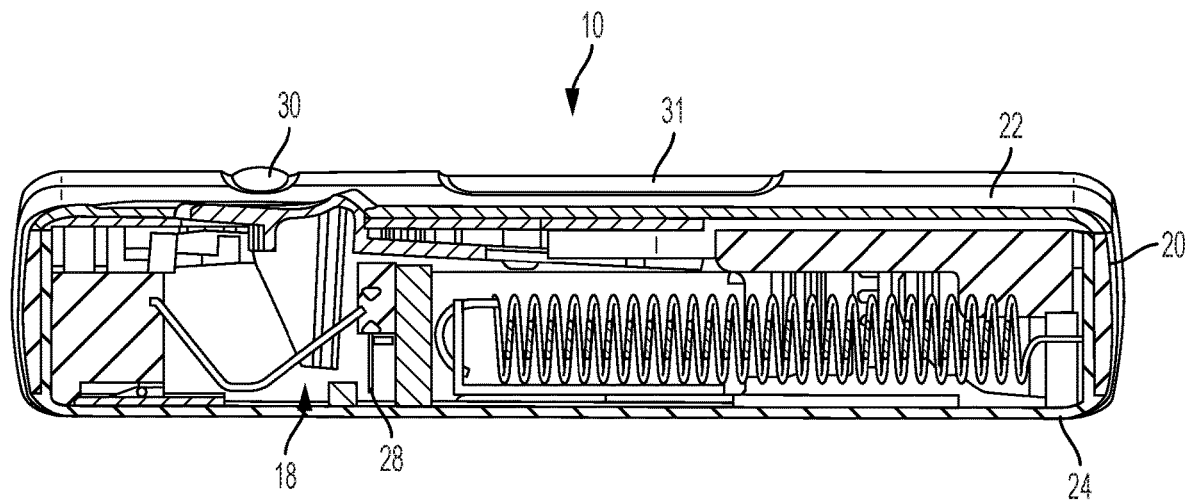
FIG. 9 is a front, cross-sectional view of the drug delivery system of FIG. 1, showing the drug delivery system in an initial actuation position.

Referring to FIGS. 4-6, during a pre-use position of the system 10, the container 14 is spaced from the drive assembly 12 and the valve assembly 16 and the needle 28 is in a retracted position. During the initial actuation of the system 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube (not shown) or other suitable arrangement. The drive assembly 12 is configured to engage a stopper 34 of the container 14, which will initially move the entire container 14 into engagement with the valve assembly 16 due to the incompressibility of the fluid or medicament within the container 14. The initial actuation of the system 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the system 10.

Figure 10:
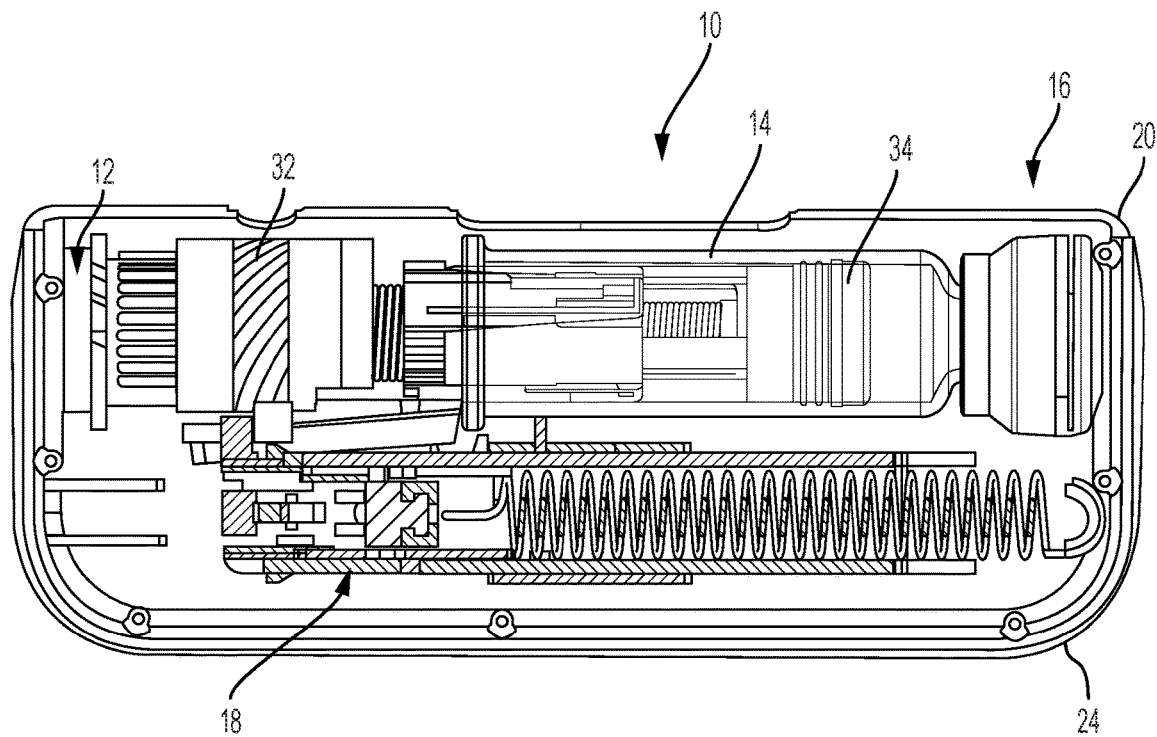
FIG. 10 is a top view of the drug delivery system of FIG. 1, showing a top portion of the housing removed and the drug delivery system in a use position.
Figure 11:
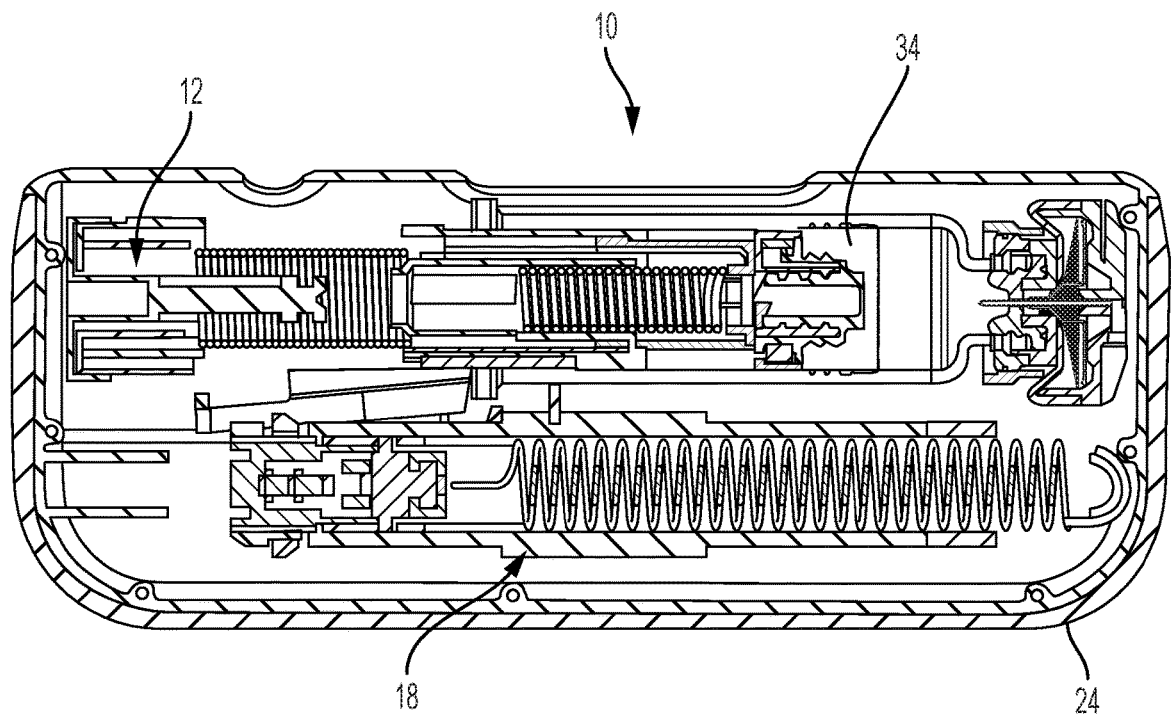
FIG. 11 is a top, cross-sectional view of the drug delivery system of FIG. 1, showing the drug delivery system in a use position.
Figure 12:
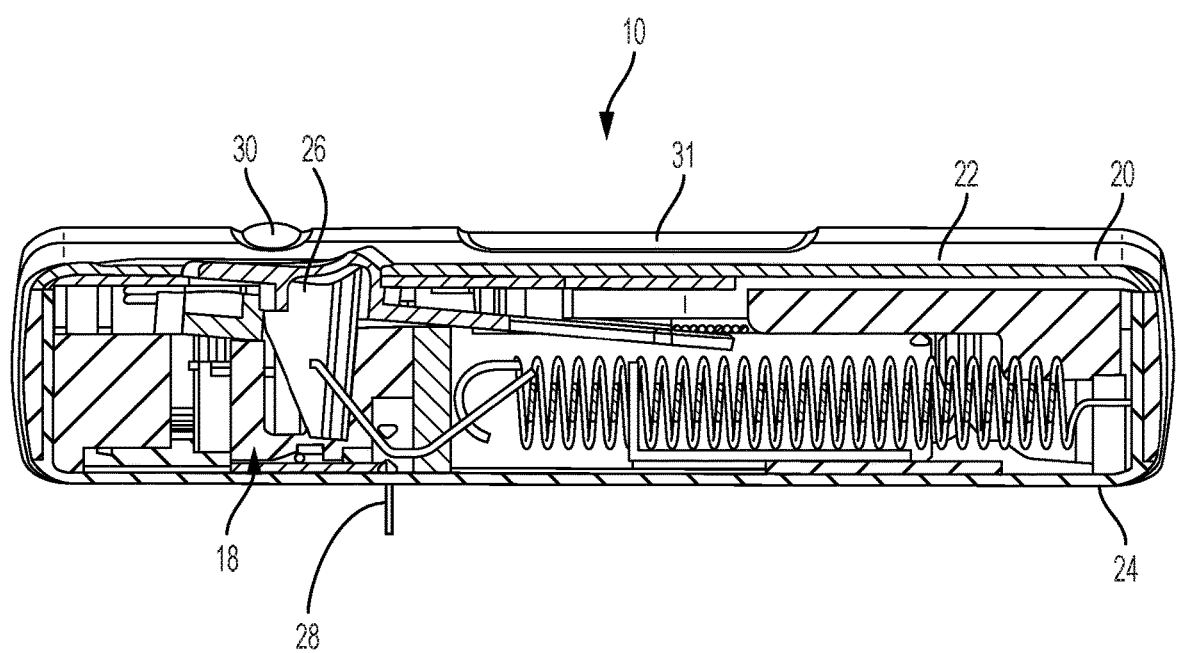
FIG. 12 is a front, cross-sectional view of the drug delivery system of FIG. 1, showing the drug delivery system in a use position.
Figure 13:
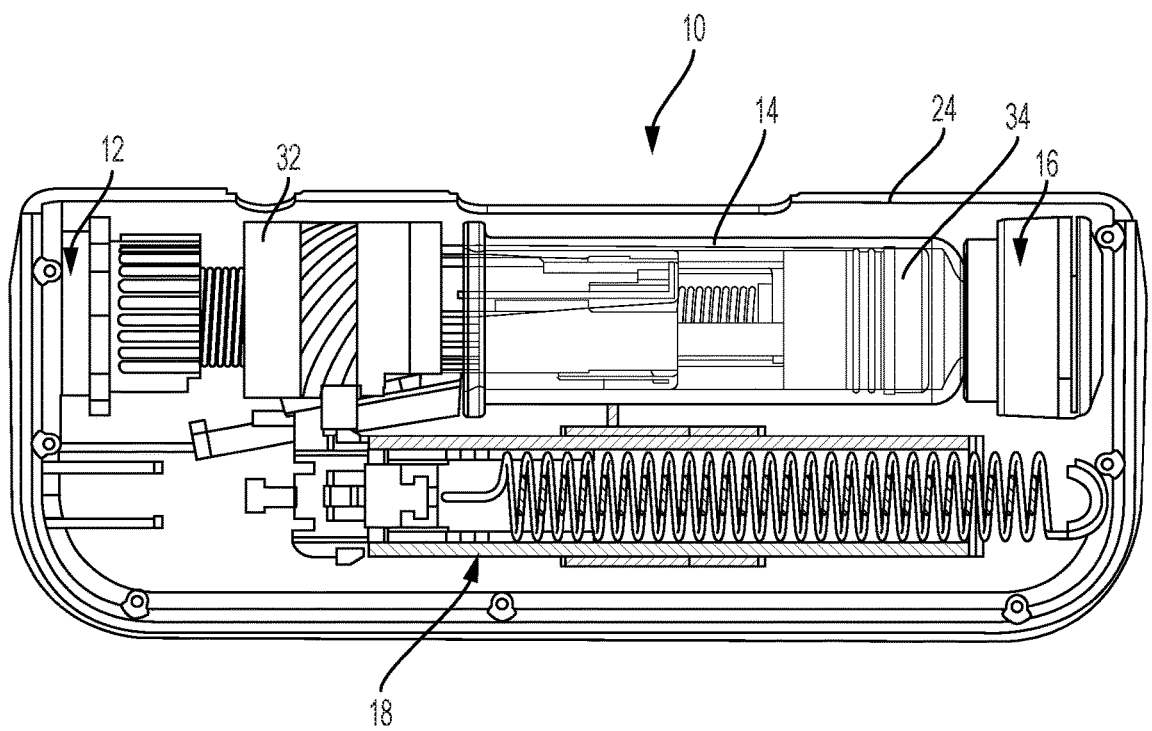
FIG. 13 is a top view of the drug delivery system of FIG. 1, showing a top portion of the housing removed and the drug delivery system in a post-use position.
Figure 14:
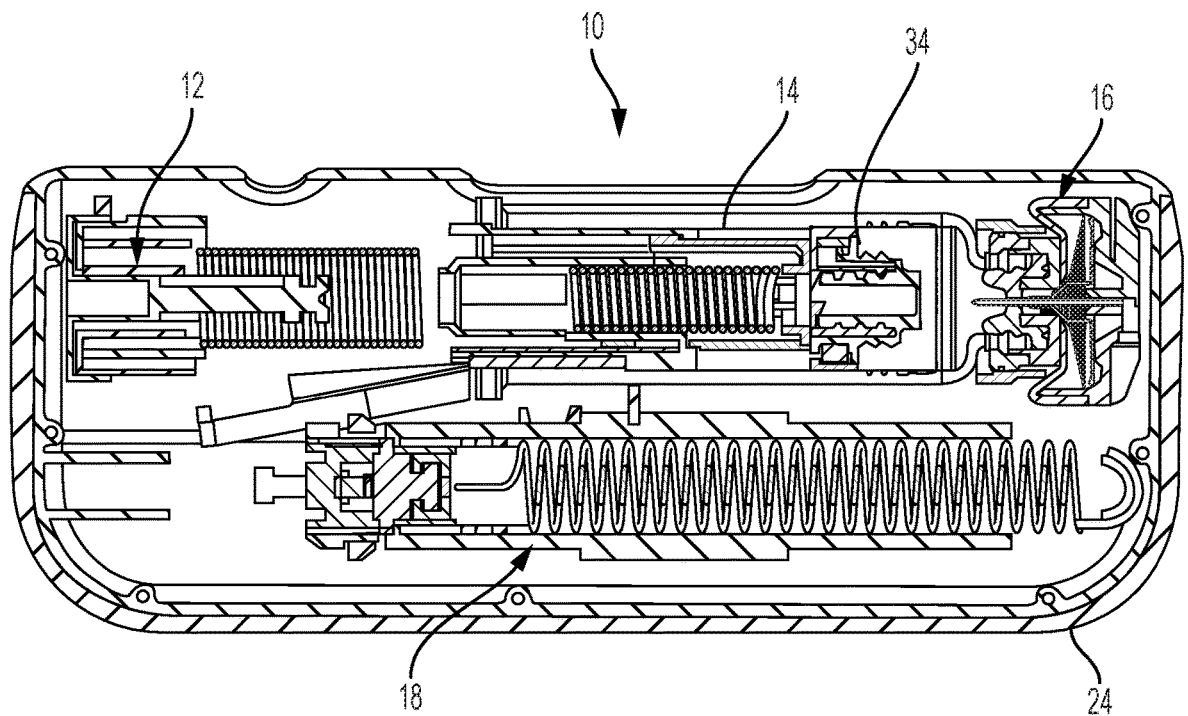
FIG. 14 is a top, cross-sectional view of the drug delivery system of FIG. 1, showing the drug delivery system in a post-use position.
Figure 15A:
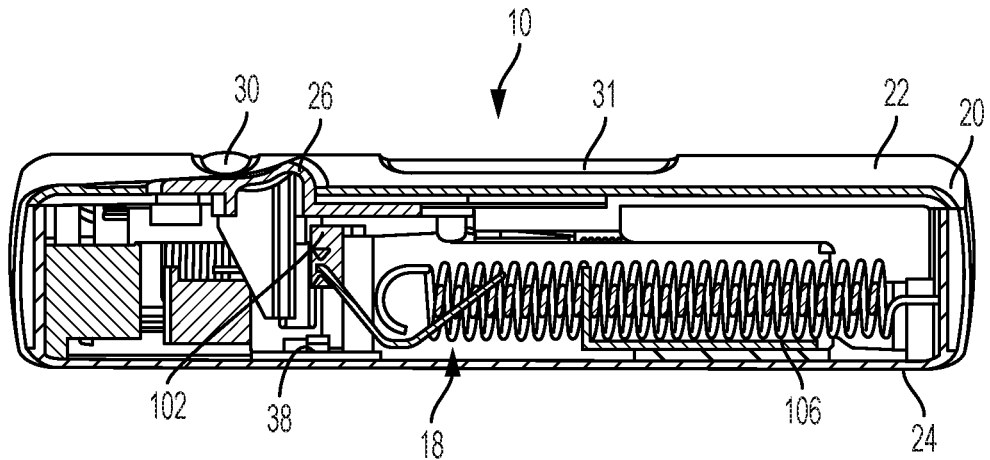
FIG. 15A is a front, cross-sectional view of the drug delivery system of FIG. 1, showing the drug delivery system in a post-use position.
Figure 15B:
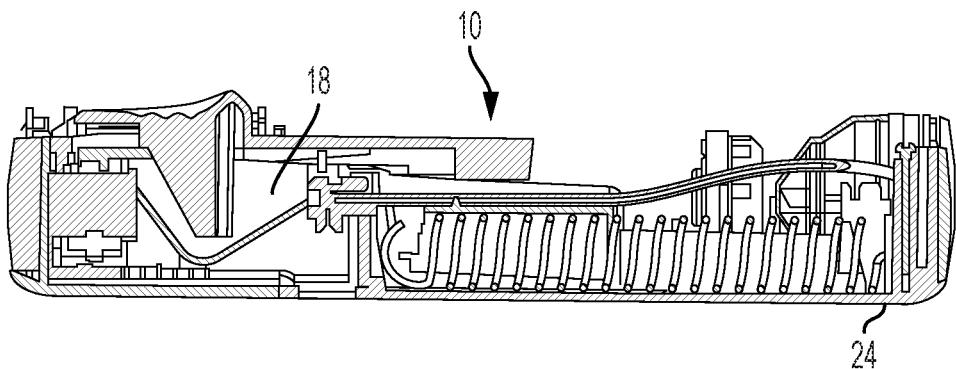
FIG. 15B is a front, cross-sectional view of the drug delivery system of FIG. 1, showing a pad with the drug delivery system in a pre-use position.
Figure 15C:
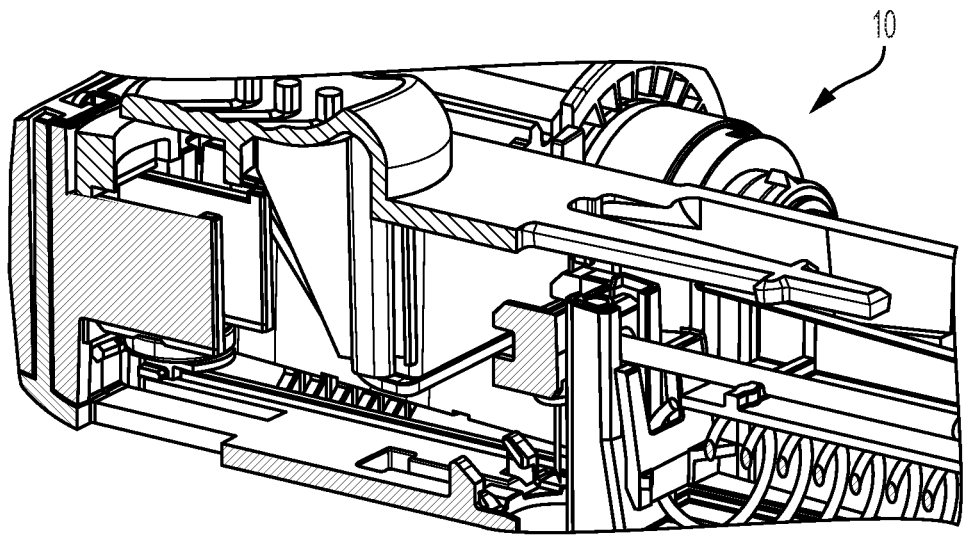
FIG. 15C is a perspective, cross-sectional view of the drug delivery system of FIG. 1, showing a pad with the drug delivery system in a pre-use position.
Figure 15D:
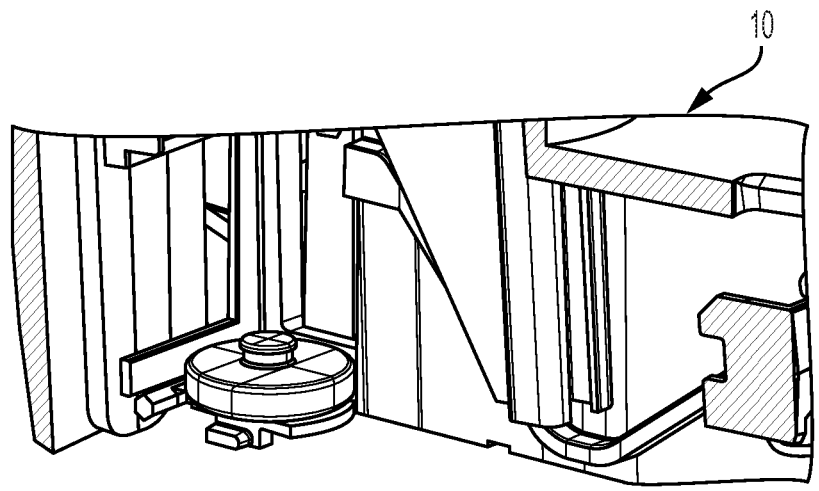
FIG. 15D is a perspective, cross-sectional view of the drug delivery system of FIG. 1, showing a pad with the drug delivery system in a pre-use position.
Figure 16:
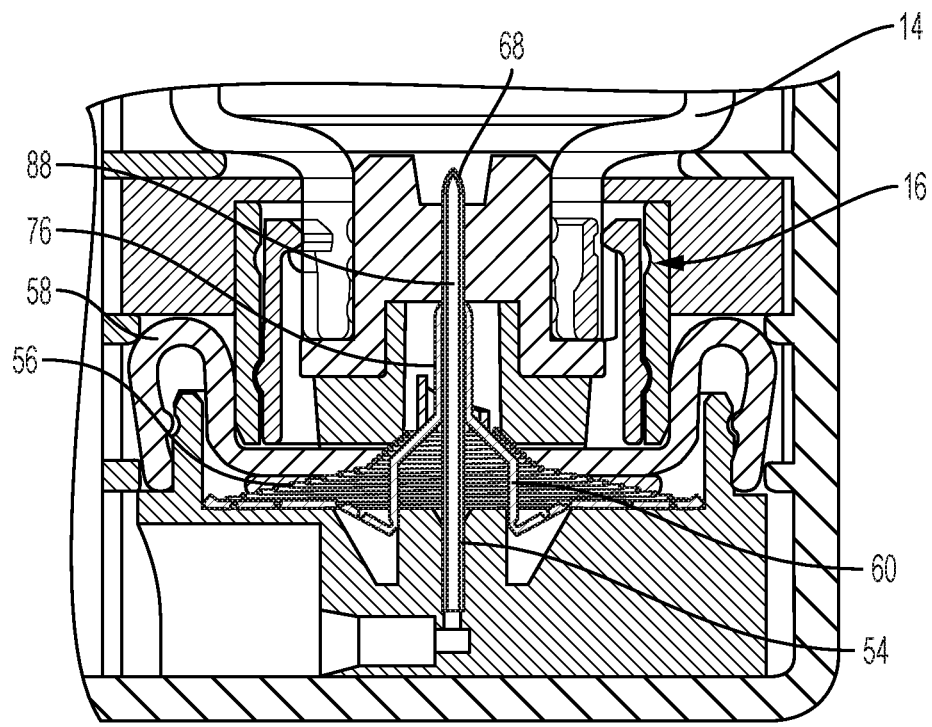
FIG. 16 is a partial cross-sectional view of the drug delivery system of FIG. 1, showing a valve assembly.

During the use position of the system 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the system 10, shown in FIGS. 13-15, the needle 28 is in the retracted position and engaged with a pad 38 to seal the needle 28 and prevent any residual flow of fluid or medicament from the container 14.

Referring to FIGS. 17-20B, as discussed above, the valve assembly 16 operates to facilitate fluid communication between the container 14 and the needle actuator assembly 18. The valve assembly 16 includes a valve housing 52, a cannula 54, a pierce plate 56, and a valve boot 58. As discussed below, the valve assembly 16 may also include a valve sleeve 60. The valve housing 52 has a first side 62 and a second side 64 positioned opposite from the first side 62. The valve housing 52 may be formed integrally with the housing 20 of the system 10 or may be formed as a separate component. The cannula 54 has a first end 66 and a second end 68 positioned opposite from the first end 66. The cannula 54 defines a central passageway 70. The first end 66 of the cannula 54 is sharp and configured to pierce a septum of the container 14. The second end 68 of the cannula 54 is received by and secured to the valve housing 52. The valve housing 52 is in fluid communication with the needle actuator assembly 18 via tubing (not shown) to form a fluid flow path from the cannula 54 to the needle actuator assembly 18.

Figure 17:
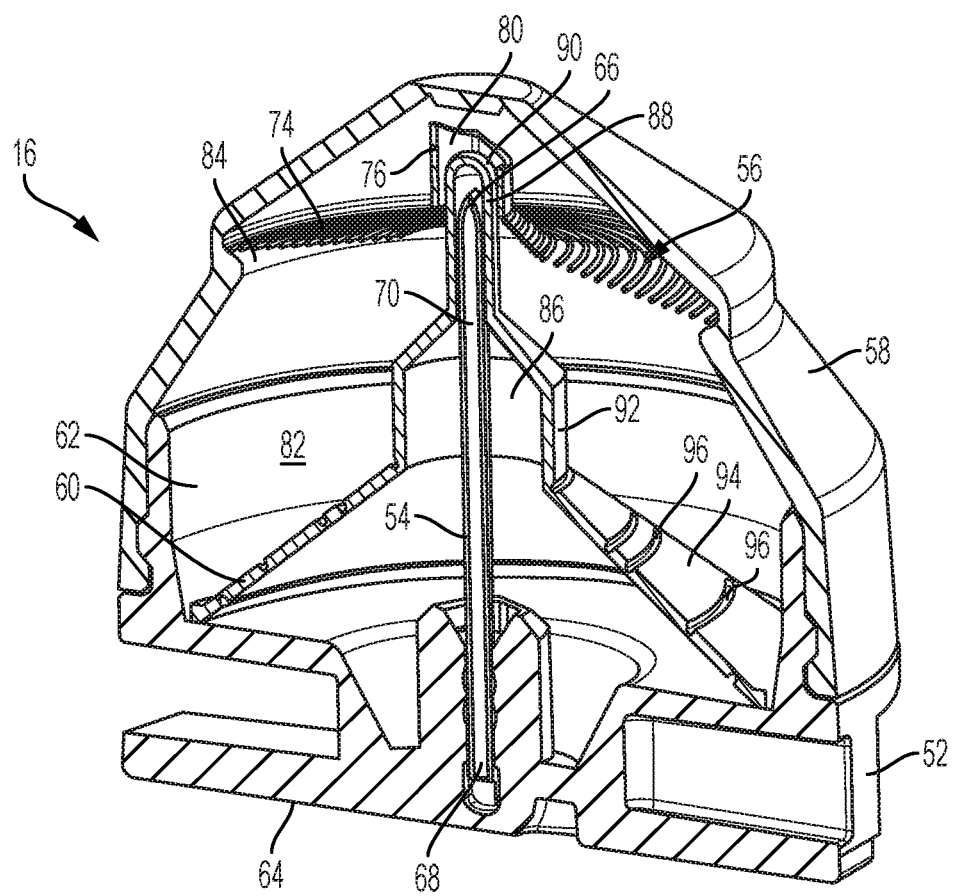
FIG. 17 is a perspective, cross-sectional view of a valve assembly of the drug delivery system of FIG. 1.
Figure 18:
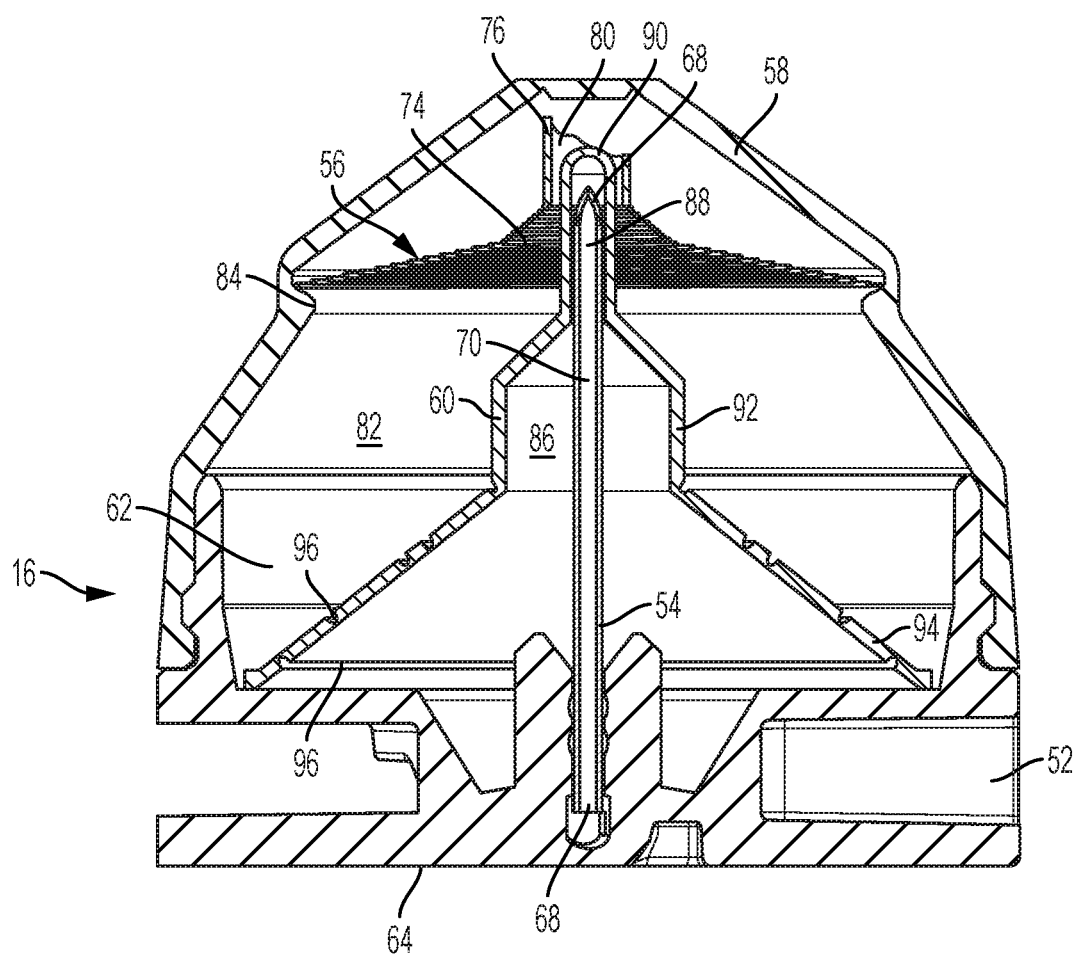
FIG. 18 is a front, cross-sectional view of the valve assembly of the drug delivery system of FIG. 1.
Figure 19:
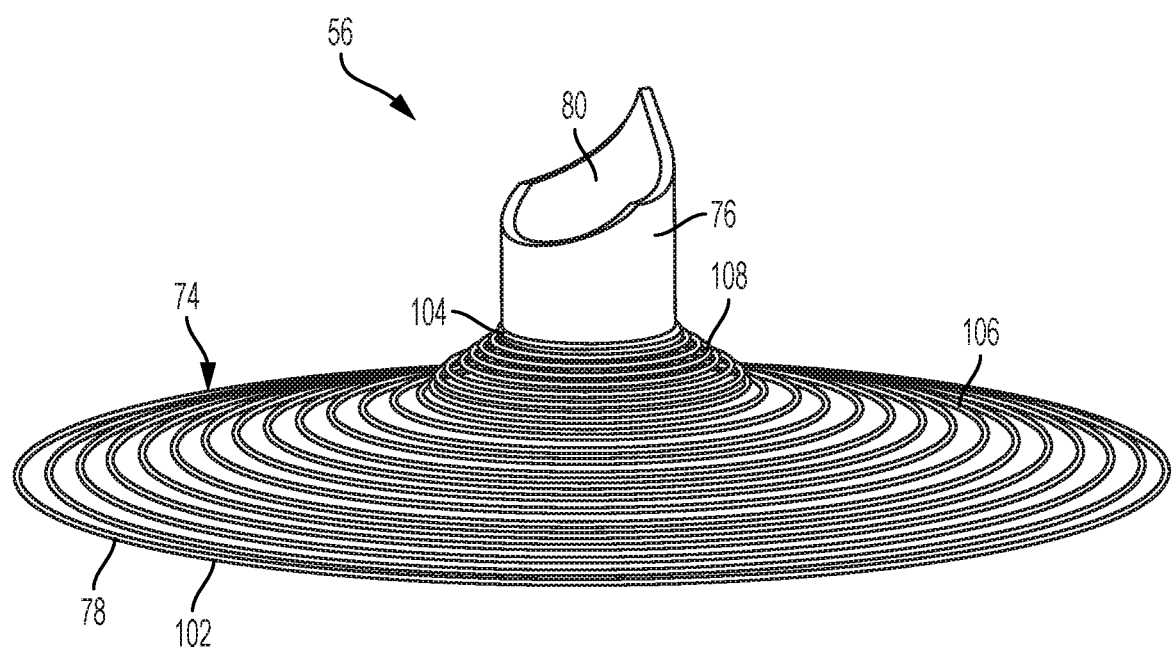
FIG. 19 is a perspective view of a pierce plate of the valve assembly of FIG. 17 according to one aspect or embodiment of the present application.
Figure 20A:
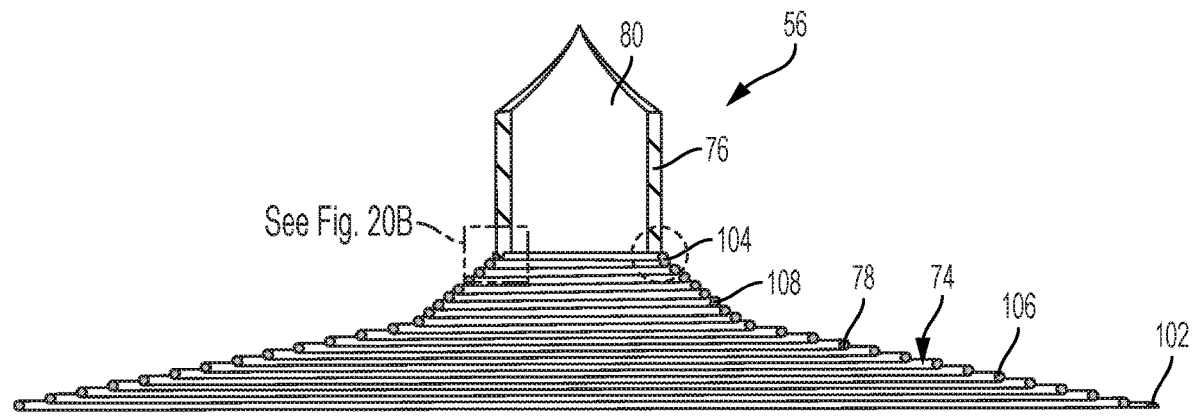
FIG. 20A is a cross-sectional view of the pierce plate of FIG. 19.
Figure 20B:
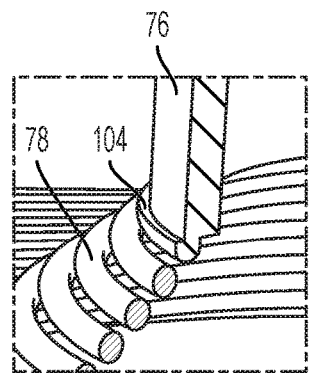
FIG. 20B is a partial cross-sectional view of the pierce plate of FIG. 19.

Referring again to FIGS. 17-20B, the pierce plate 56 includes a body 74 and a piercing member 76 extending from the body 74. The body 74 is formed from a coiled elongate member 78 with the piercing member 76 defining a central passageway 80 configured to receive the cannula 54. The valve boot 58 is connected to the valve housing 52 and defines an interior space 82. The valve boot 58 may be formed from an elastomeric material, although other suitable materials or combination of materials may be utilized. The valve boot 58 is configured to move from a pre-use position where the first end 66 of the cannula 54 and the piercing member 76 of the pierce plate 56 are received within the interior space 82 to a use position where the piecing member 76 of the pierce plate 56 and the first end 66 of the cannula 54 extend outside of the valve boot 58 and the interior space 82. The pre-use position of the valve boot 58 and the valve assembly 16 is shown in FIG. 18. Although not shown, the use position of the valve boot 58 and the valve assembly 16 will be similar to the use position of the valve assembly 16 shown in FIG. 16. In the use position, the pierce plate 56 is engaged with the valve housing 52 with the piercing member 76 piercing the valve boot 58 and a foil seal (not shown) on the container 14 and with the cannula 54 piercing a septum of the container 14 to provide fluid communication with the interior of the container 14 and the cannula 54. The valve boot 58 includes a projection 84 extending radially inward with the pierce plate 56 engaged with the projection 84. The projection 84 may be annular with the projection 84 engaging the body 74 of the pierce plate 56. In the pre-use position of the valve boot 58, as shown in FIG. 17, the pierce plate 56 is spaced from the valve housing 52 via the engagement of the projection 84 of the valve boot 58 with the pierce plate 56. During engagement with the cartridge 14, the valve boot 58 will collapse with the pierce plate 56 moving downward toward the valve housing 52.

Referring to FIGS. 17 and 18, the valve sleeve 60 is positioned within the interior space 82 defined by the valve boot 58. The valve sleeve 60 defines a cannula space 86 and is configured to move from a pre-use position where the first end 66 of the cannula 54 is received within the cannula space 86 to a use position where the first end 66 of the cannula 54 extends outside of the valve sleeve 60 and the cannula space 86. The valve sleeve 60 may be formed from an elastomeric material, such as a rubber material, although other suitable materials or combination of materials may also be utilized. In one aspect or embodiment, the valve sleeve 60 is a thin film of a non-rubber material. The valve sleeve 60 includes a first cylindrical portion 88 having a convex tip 90, a second portion 92 extending from the first portion 88, and a third frustoconical portion 94 extending from the second portion 92. The second portion 92 is frustoconical and cylindrical. The third portion 94 of the valve sleeve 60 may include one or more recessed portions 96 to facilitate the collapse and deformation of the valve sleeve 60. Upon engagement of the valve assembly 16 with the container 14, the valve sleeve 60 will retract with the first end 66 of the cannula 54 extending through the valve sleeve 60.

The valve sleeve 60 is configured to ensure the cannula 54 and flow path of the system 10 remain free from contamination during operation of the system 10. During operation of the system 10, as discussed above, the container 14 is moved into engagement with the valve boot 58 to collapse the valve boot 58 with the piercing member 76 of the pierce plate 56 puncturing the foil seal of the container 14 and the valve boot 58 to form respective chads or flaps (not shown). The valve sleeve 60 prevents any contamination present on the container 14 and valve boot 58 from being discharged or flung from the container 14 or valve boot 58 onto or into the cannula 54. The valve sleeve 60 also shields the cannula 54 from contact with the chads or flaps formed by the piercing member 76 and minimizes the surface area of the closure 36 of the container 14 through which the cannula 54 must pass through. The valve sleeve 60 is also configured to prevent contamination caused by the depressurization of the valve boot 58 when the valve boot 58 is compressed and subsequently pierced by the piercing member 76 by preventing the settling of entrained contamination onto the external and internal surfaces of the cannula 54.

Referring again to FIGS. 17-20B, as discussed above, the coiled elongate member 78 has a first end 102 and a second end 104 axially spaced from the first end 102 with the second end 104 of the coiled elongate member 78 configured to move toward the first end 102 of the coiled elongate member 78. The coiled elongate member 78 is frustoconical. More specially, the coiled elongate member 78 includes a first frustoconical portion 106 and a second frustoconical portion 108. The first frustoconical portion 106 may have a larger angle than the second frustoconical portion 108. The piercing member 76 is connected to the second end 104 of the coiled elongate member 78. The piercing member 76 may be connected to the second end 104 of the coiled elongate member 78 via an adhesive or welding, although other suitable securing arrangements may be utilized. The coiled elongate member 78 may be a metal wire that is coiled around a mandrel to form the shape of the body 74 of the pierce plate 56. In one aspect, the metal wire may be formed of a material that allows for a controlled collapse while preventing collapse onto itself. The metal wire can be deformed under low loading conditions and then return to its original shape.

In one aspect, the metal wire may be formed from a shape memory alloy, such as Nitinol, although other suitable materials or combination of materials may be utilized. Shape memory alloys are readily formed into a desired shape or configuration with the shape, size, and dimensions being readily altered without significant costs in tooling. The body 74 of the pierce plate 56 acts as a spring and shock absorber during engagement of the cartridge 14 with the valve assembly 16 to more efficiently dissipate the force of the cartridge 14 contacting the valve assembly 16. Due to the strength of the coiled elongate member 78, however, the piercing functionality of the piercing member 76 is not compromised. The strength and stiffness of the body 74 of the pierce plate 56 can be readily adjusted by changing the number of revolutions of the coiled elongate member 78. The coiled elongate member 78 of the pierce plate 56 includes approximately 22 revolutions or coils, although any other suitable configurations may be utilized.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A valve assembly for a drug delivery device, the valve assembly comprising:
   a valve housing having a first side and a second side positioned opposite from the first side;
   a cannula having a first end and a second end positioned opposite the first end, the cannula defining a central passageway;
   a valve boot connected to the valve housing and defining an interior space, the valve boot is configured to move from a pre-use position where the first end of the cannula is received within the interior space to a use position where the first end of the cannula extends outside of the valve boot and the interior space; and
   a valve sleeve defining a cannula space, the valve sleeve is configured to move from a pre-use position where the first end of the cannula is received within the cannula space to a use position where the first end of the cannula extends outside of the valve sleeve and the cannula space, wherein the valve sleeve is positioned within the interior space defined by the valve boot.

2. The valve assembly of claim 1, wherein the valve sleeve comprises an elastomeric material.

3. The valve assembly of claim 1, wherein the valve sleeve comprises a first cylindrical portion having a convex tip, a second portion extending from the first portion, and a third frustoconical portion extending from the second portion.

4. The valve assembly of claim 3, wherein the second portion of the valve sleeve comprises a frustoconical section and a cylindrical section.

5. The valve assembly of claim 3, wherein the third portion of the valve sleeve comprises at least one recessed portion configured to facilitate a collapse and deformation of the valve sleeve.

6. The valve assembly of claim 1, wherein the valve sleeve comprises a rubber material.

7. The valve assembly of claim 1, wherein the valve boot comprises an elastomeric material.

8. The valve assembly of claim 1, further comprising a pierce plate comprising a body and a piercing member extending from the body, wherein the piercing member of the pierce plate is received within the interior space of the valve boot when the valve boot is in the pre-use position, and wherein the piercing member of the pierce plate extends outside of the valve boot and the interior space when the valve boot is in the use position.

9. A drug delivery device comprising:
a housing;
a cartridge received within the housing, the cartridge configured to receive a medicament;
a drive assembly received within the housing and configured to engage the cartridge and dispense medicament from the cartridge;
a needle actuator assembly received within the housing, the needle actuator assembly comprising a patient needle configured to pierce a patient's skin; and
a valve assembly, comprising:
  a valve housing having a first side and a second side positioned opposite from the first side,
  a cannula having a first end and a second end positioned opposite the first end, the cannula defining a central passageway,
  a valve boot connected to the valve housing and defining an interior space, the valve boot is configured to move from a pre-use position where the first end of the cannula is received within the interior space to a use position where the first end of the cannula extends outside of the valve boot and the interior space, and
  a valve sleeve defining a cannula space, the valve sleeve is configured to move from a pre-use position where the first end of the cannula is received within the cannula space to a use position where the first end of the cannula extends outside of the valve sleeve and the cannula space,
wherein the valve sleeve is positioned within the interior space defined by the valve boot.

* * * * *